United States Patent
Peng et al.

[11] Patent Number: 5,869,025
[45] Date of Patent: Feb. 9, 1999

[54] TRIPODAL AROMATIC HETEROCYCLE CARBOXAMIDE MRI CONTRAST AGENTS

[75] Inventors: Wei-Jen Peng, Corpus Christi, Tex.; David E. Reichert, St. Louis, Mo.

[73] Assignees: Hoechst Celanese Corporation, Somerville, N.J.; Washington University, St. Louis, Mo.

[21] Appl. No.: 915,808

[22] Filed: Aug. 21, 1997

[51] Int. Cl.⁶ ............. A61B 5/055; A61K 51/00; C07D 401/00
[52] U.S. Cl. .............. 424/9.361; 424/9.36; 424/1.65; 546/2; 546/5; 546/268.1; 546/261
[58] Field of Search ............. 424/9.361, 9.36, 424/9.364, 1.65; 534/10, 14, 15, 16; 546/2, 5, 6, 261, 263, 264, 265, 266, 268.1; 540/465, 471; 544/63, 124; 548/101

[56] References Cited

U.S. PATENT DOCUMENTS

| | | |
|---|---|---|
| 4,001,323 | 1/1977 | Felder et al. . |
| 4,250,113 | 2/1981 | Nordal et al. . |
| 4,396,598 | 8/1983 | Lin . |
| 4,647,447 | 3/1987 | Gries et al. . |
| 4,687,658 | 8/1987 | Quay . |
| 4,687,659 | 8/1987 | Quay . |
| 4,719,098 | 1/1988 | Weinmann et al. . |
| 4,826,673 | 5/1989 | Dean et al. . |
| 4,837,169 | 6/1989 | Toner . |
| 4,957,939 | 9/1990 | Gries et al. . |
| 4,960,895 | 10/1990 | Ohkawa . |
| 5,130,437 | 7/1992 | Rocklage et al. . |
| 5,216,134 | 6/1993 | Mukkala et al. . |
| 5,252,740 | 10/1993 | Hale et al. . |
| 5,405,601 | 4/1995 | Dunn et al. . |
| 5,457,186 | 10/1995 | Mukkala et al. . |
| 5,559,214 | 9/1996 | Delecki et al. . |
| 5,571,897 | 11/1996 | Takalo et al. . |
| 5,608,059 | 3/1997 | Wear et al. . |
| 5,624,901 | 4/1997 | Raymond et al. . |

OTHER PUBLICATIONS

Chemical Communications, No. 14 (1992), Adolfsson et al.
Chemical Communications, No. 22 (1992), Adolfsson et al.
Organic Chemistry, Fourth Edition of T.W. Graham Solomons 1988.

*Primary Examiner*—Gary E. Hollinden
*Assistant Examiner*—Michael G. Hartley
*Attorney, Agent, or Firm*—James J. Mullen; Stuart D. Frenkel; John J. Piskorski

[57] ABSTRACT

A composition of matter having the formula

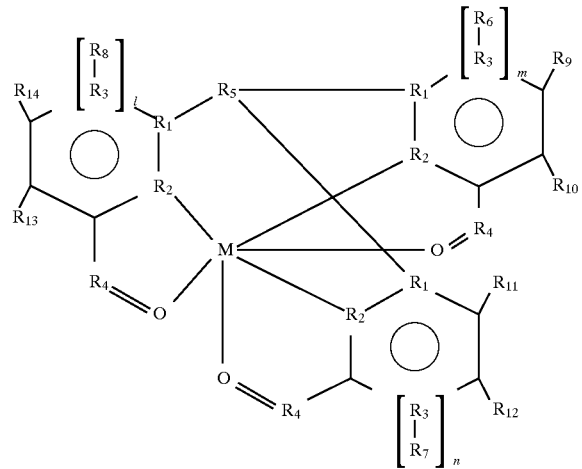

wherein $R_1$–$R_{14}$, M, l, m, and n are defined herein and which have application as MRI contrasting agents.

9 Claims, No Drawings

TRIPODAL AROMATIC HETEROCYCLE CARBOXAMIDE MRI CONTRAST AGENTS

FIELD OF THE INVENTION

This invention relates to magnetic resonance imaging (MRI), X-ray imaging, and radiopharmaceuticals. More particularly the invention relates to methods and compositions for enhancing MRI, X-ray imaging, and radio pharmaceuticals, ligands therefor, and precursors of said ligands.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast agent which is substantially radiopaque. In conventional proton MRI diagnostics, increased contrast of internal organs and tissues may be obtained by administering compositions containing paramagnetic metal species which increase the relaxation rate of surrounding protons. IN ultrasound diagnostics, improved contrast is obtained by administering compositions having acoustic impedances different than that of blood or other tissues.

The recently developed technique of MRI encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that is has found application as a means of mapping the internal structure of the body as a result of the original suggestion of Lauterbur (*Nature*, 242, 190–191 [(1973)]. The fundamental lack of any known hazard associated with the level of magnetic and radio-frequency fields that are employed renders it possible to make repeated scans on vulnerable individuals. In addition to standard scan plans (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin when placed in an applied magnetic field (B, expressed generally in units of gauss of Tesla [$10^4$ gauss]) align in the direction of the field. In the case of protons, these nuclei precess at a frequency, f, of 42.6 MHZ, at a field strength of 1 Tesla. At this frequency, an RF pulse of radiation will excite the nuclei and can be considered to tip the net magnetization of the field direction, the extent of this rotation being determined by the pulse duration and energy. After the RF pulse, the nuclei "relax" or return to equilibrium with the magnetic field, emitting radiation at the resonant frequency. The decay of the emitted radiation characterized by two relaxation times, i.e., $T_1$, the spin-lattice relaxation time or longitudinal relaxation time, that is, the time taken by the nuclei to return to equilibrium along the direction the externally applied magnetic field, and $T_2$, the spin-spin relaxation time associated with the dephasing of the initially coherent precession of individual proton spins. These relaxation times have been established for various fluids, organs and tissues in different species of mammals.

An MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density pulse sequence and flow) may contribute to the MRI signal.

By reason of its sensitivity to subtle physiochemical differences between organs and/or tissues, it is believed that MRI may be capable of differentiating different tissue types in detecting diseases which induce physiochemical changes that may not be detected by X-ray or CT which are only sensitive to differences in electron density of tissue.

As noted above two of the principal imaging parameters are the relaxation times, $T_1$ and $T_2$. For protons (or other appropriate nuclei), these relaxation times are influenced by environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporation these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic numbers of 21 to 29, 42 to 44 and 58 to 70 have been found effective as MRI contrasting agents. Examples of suitable ions include chromium (III), manganese (II), manganese (III), iron, (II), iron (III), cobalt (II), nickel (II), copper (II), praseodymium (III), neodymium (III), samarium (III), and ytterbium (III). Because of their very strong magnetic moments, gadolinium (III), terbium (III), dysprosium (III), holmium (III), and erbium (III) are preferred. Gadolinium (III) ions have been particularly preferred as MRI contrasting agents.

Typically, paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylenetriaminepentaacetic acid ("DTPA"). Paramagnetic ions, such as gadolinium (III), have been found to form strong complexes with DTPA, ethylenediamine-tetra acetic acid ("EDTA"), and with tetraazacyclododecane-N,N',N'',N'''-tetra acetic acid ("DOTA").

These complexes do not dissociate substantially in physiological aqueous fluids. The gadolinium complex of DTPA has a net charge of −2, whereas the gadolinium complex of EDTA or DOTA has a net charge of −1, and both are generally administered as soluble salts. Typical salts are sodium and N-methylglucamine. The administration of salt is attended by certain disadvantages. These salts can raise the in vivo ion concentration and cause localized disturbances in osmality, which in turn, can lead to edema and other undesirable reactions.

Efforts have been made to design new ionic and neutral paramagnetic metals complexes which avoid or minimize the above mentioned disadvantages. In general, this goal can be achieved by converting one or more of the free carboxylic acid groups of the complexing agents to neutral, non-ionizable groups, for example, S. C. Quy, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxy-alkylamide derivatives of DTPA and their use as complexing agents for paramagnetic ions. It can also be achieved by covalent attachment of organic cations of the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al. AJR 142,679 (March 1984) and Brasch, et al. AJR, 142,625 (March 1984).

Finally, toxicity of paramagnetic metal complexes is greatly affected by the nature of the complexing agents. IN vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Caheris et al., *Magnetic Resonance Imaging*, 8:467 (1990) and Oksendal, et al., *JMRI*, 3:157 (1993).

A need continues to exist for new and structurally diverse compounds for use as imaging agents including ligands therefor and precursor ligands. There is a further need to develop highly stable complexes with good relaxivity and osmolar characteristics.

Thus, there is always a need for new and more effective agents requiring lower dosage use, lower toxicity, higher resolution and more organ/disease specificity.

DESCRIPTION OF THE PRIOR ART

The following prior art references are disclosed for informational purposes.

U.S. Pat. No. 4,001,323 discloses water-soluble non-ionizing hydroxy-containing amide derivatives of 2,4,6-triiodoisophthalic acid for use as radiopaque materials.

U.S. Pat. No. 4,250,113 discloses new amides as X-ray contrast agents.

U.S. Pat. No. 4,396,598 discloses triiodoisophthalamide X-ray contrast agents.

U.S. Pat. No. 4,647,447 discloses new paramagnetic contrast agents.

U.S. Pat. No. 4,687,659 discloses homologs of diamide-DTPA-paramagnetic compounds as contrast agents for MR imaging.

U.S. Pat. No. 4,719,098 discloses enteral contrast medium useful for nuclear magnetic resonance imaging.

U.S. Pat. No. 4,957,939 discloses sterile pharmaceutical compositions of gadolinium chelates useful as enhancing NMR imaging.

U.S. Pat. No. 5,405,601 discloses functionalized tripodal ligands for imaging applications.

*Proc. Natl. Acad. Sci.* USA, Vol 93, pp 6610–6615, June 1996, Medical Sciences; Young et al. disclose gadolinium (III) texaphyrin: a tumor selective radiation sensitizer that is detectable by MRI.

H. Reimlinge, *Chem. Ber.*, 92, 970 (1995) discloses synthesis of substituted pyrazoles.

Kamitori Y. et al, *Heterocycles*, 38 (1), 21 (1994) discloses synthesis of substituted pyrazoles.

Sauer, D. R. et al., *Carbohyde Res*, 241 (1993) 71 discloses synthesis of substituted pyrazoles.

Amoroso, A. J. et al, *J. Chem. Soc., Chem. Comm.* 1994, 2751, discloses a general synthesis of ligands.

Campbell, A. D. et al., *Aust. J. Chem.* 1971, 24, 377–83 discloses a general synthesis of ligands.

Kametani, T., *Tetrahedron*, 1970, 26, 5753 discloses a general synthesis of ligands.

All of the above cited prior art and any other references mentioned herein are incorporated herein by reference in their entirety.

SUMMARY OF THE INVENTION

The present invention provides novel compositions of matter having the formula wherein $R_1$–$R_{14}$, M, l, m and n are defined herein and which have applications, for example, as MRI contrasting agents.

Compositions comprising the above formula (I) wherein M is a radioactive metal, ion, a paramagnetic ion, or a metal ion capable of absorbing X-rays are also provided for use as radiopharmaceuticals, magnetic resonance imaging, and X-ray contrast agents, respectively.

Diagnostic compositions comprising the compounds of the invention are also provided. Methods of performing diagnostic procedures with compositions of the invention are also disclosed. The methods comprise administering to a patient an effective amount of the compositions of the invention and subjecting the patient to an imaging procedure.

DETAILS DESCRIPTION OF THE INVENTION

There is provided, in one part of the present invention, new and structurally diverse compositions of matter having the formula

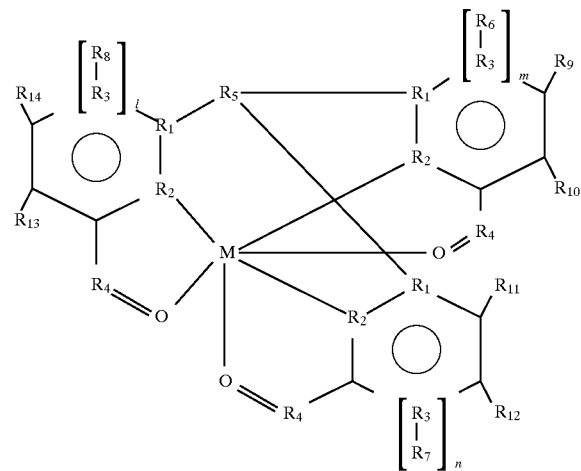

wherein:
l, m and n are independently 0 or 1
$R_1$ is C or N
$R_2$ is N, O, or S
$R_3$ is C
$R_4$ is C—N $(R_{15})(R_{16})$
$R_5$ is selected from the group consisting of
  (a) P
  (b) P=O
  (c) $B(R)^-M'$
  (d) N
  (e) $N(CH_2)$
  (f) $N[C(O)]_3$
  (g) $N[CH_2C(O)]_3$
  (h) CH
  (I) COR
  (j) $COC(O)N(R)_2$
  (k) $C(CH_2OR)(CH_2)_3$
  (l) SiR
  wherein R is selected from the group consisting of
    (I) H
    (ii) $C_1-C_{20}$ alkyl
    (iii) hydroxyalkyl $(C_1-C_{20})$
    (iv) $CH_2CH(OH)CH_2(O\ CH_2CH(OH)CH_2)_nOH$ (n=0–10)
    (v) $CH_2CH_2(O\ CH_2CH_2)_nOH$ (n=0–10)
    (vi) ribose
    (vii) glucose
    (viii) peptide or polypeptide
    (ix) $PO_3^{2-}2M'$
  and M' is $Na^+$ or meglumine
$R_6-R_{14}$ are each independently selected from the group consisting of (a) R
(b) OR
(c) $NR_2$
(d) NHC(O)R
(e) $COO^-M'$
(f) $C(O)N(R)_2$
(g) $SO_3^-M'$
wherein R and M' are defined as above, and
M is a suitable metal ion such as a metal ion of the lanthamide series having an atomic number of 57 or 71, or of a transition metal of an atomic number of 21–29, 42, or 44, with the proviso that $R_{15}$ and $R_{16}$ are each the same as R defined above, except (ix), and $R_{15}$ and $R_{16}$, respectively, are each the same on each ring.

In the above formula I, M is selected from the group consisting of chromium (III), manganese (II), iron (III), iron (II), cobalt (II), nickel (II), copper (II), praseodymium (III), neodymium (III), samarium (III), ytterbium (III), gadolinium (III), terbium (III), dysprosium (III), holmium (III), erbium (III), lanthamium (III), gold (III), lead (II), bismuth (III), lutetium (III), and europium (III).

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris(hydroxymethyl) methyl and 2-hydroxy-1-hydroxymethyl-ethyl. Suitable alkoxyalkyl group include methoxymethyl, 2,3-dimethoxypropyl, tis(methoxymethyl) methyl, and 2-methoxy-1-methoxymethyl-ethyl.

An example of a class of compounds falling within formula (I) above include:

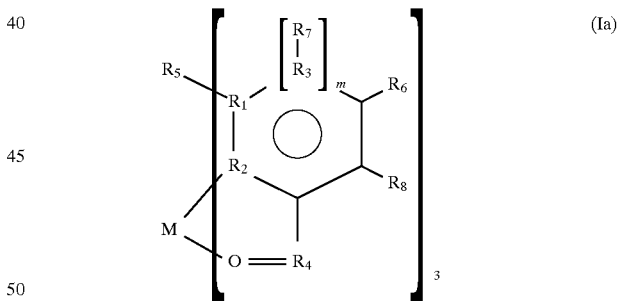

(Ia)

wherein $R_1-R_8$ and M have the same definition as in formula (I) above.

Examples of compounds falling within formula Ia include:

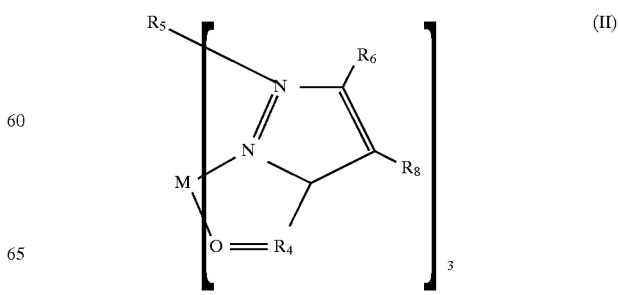

(II)

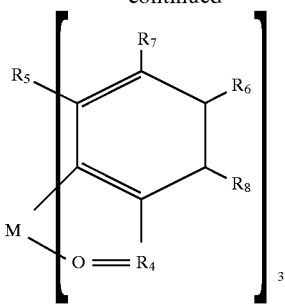 (III)

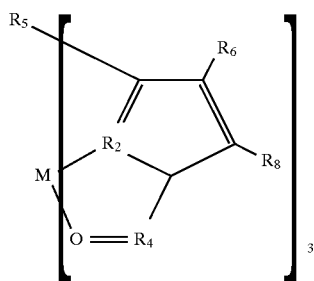 (IV)

wherein in formulae (II), (III), and (IV), $R_2$ $R_4$–$R_8$, and M have the same definition as set forth in formulae (Ia).

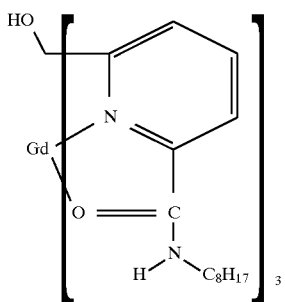 (V)

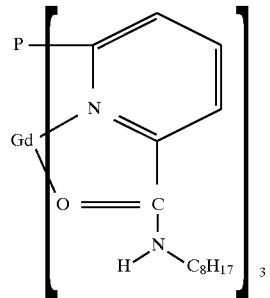 (VII)

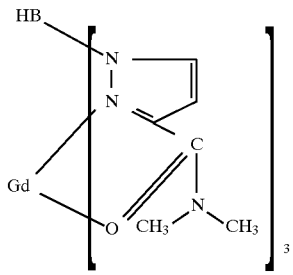 (VIII)

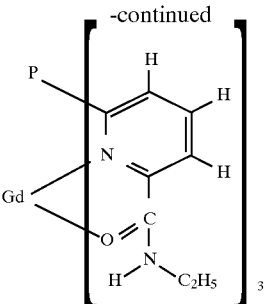 (IX)

The compositions of the present invention are suitable for use with a variety of modalities including X-rays, magnetic resonance imaging and radiopharmaceuticals.

The functionality of the $R_5$–$R_8$ groups of the compositions of the present invention afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies, a fragment of monoclonal antibody and aptamers. Specific examples of biomolecules include insulins, prostaglandins, growth factors, liposomes and nucleic acid probes. Examples of synthetic polymers include polylysine, arborols, dendrimers, cyclodextrins. The advantages of using biomolecules include enhanced tissue targeting through specificity and delivery. Coupling of the chelating moieties to biomolecules can be accomplished by several known methods (e.g., Krejacarek and Tucke *Biochem. Biophys. Rs. Comm.*, 30, 581 (1977); Hantowich, et al., *Science*, 220, 613 (1983). For example, a reactive moiety present in one of the $R_5$–$R_8$ groups is coupled with a second reactive group located on the biomolecule. Typically, a nucleophilic group is reacted with an electrophilic group to form a covalent bond between the biomolecule and chelate. Examples of nucleophilic groups include amines, anilines, alcohols, phenols, thiols, and hydrazines. Electrophilic group examples include halides, disulfides, epoxides, maleimeides, acid chlorides, anhydrides, mixed anhydrides, activated esters, imidates, isocyanates and isothiocyanates. And finally, the compositions of the invention should provide the additional advantage of being kinetically inert.

The present invention compositions with one or more central metal ions or metal ion equivalent s(M), such as paramagnetic metals praseodymium (III), neodymium (III), samarium (III), ytterbium (III), terbium (III), dysprosium (III), holmium (III)<erbium (III), iron (II), iron (III), chromium (III), cobalt (II), and nickel (II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, the novel compositions of the present invention are relatively substantially nontoxic and therefore useful for enhancing magnetic resonance images by favorable altering relaxation times $T_1$ and $T_2$ and affording improved contrast between normal and diseased tissues or organs.

The preferred compositions of the present invention are those formed with iron (II), iron (III), manganese (II), manganese (III) and gadolinium (III) as the central metal ion used (M), the compositions formed may be neutral, ionic, cationic, or zwitterionic in nature, or they may be negatively charged. The neutral compositions are generally preferred and generally appear to exhibit relatively lower toxicity as compared to ionic or negatively charged compositions. The negatively charged compositions formed by the ligands and central metal ions enumerated above may be further complexed with one or more cations or an inorganic or organic base which are physiologically tolerated. Examples of cations for further complexing include sodium, potassium, calcium, and salts of N-methylglucamine, and diethanolamine.

In addition to their utility in magnetic resonance imaging procedures, the compositions of the present invention can also be employed for delivery of either radiopharmaceuticals or heavy metals for X-ray contrast into the body. For use in diagnostic and therapeutic radiopharmaceuticals the complexed metal ion (M) must be radioactive. Radioisotopes of the elements technetium, rhenium, indium, gallium, copper, ytterbium, samarium and holmium are suitable. For use as X-ray contrast applications the complexed metal ion (M) must be able to absorb adequate amounts of the X-rays. These metal ions are generally referred to as radiopaque. Suitable elements for use as the radiopaque metal ion include lead, bismuth, gadolinium, dysprosium, holmium and praseodymium.

The compositions of the present invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, nontoxic cations. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution of suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of NMR image. Such dose may vary widely, depending upon the particular paramagnetic ion complex employed the organs or tissues which are subject of the imaging procedure, the NMR imaging procedure, the NMR imaging equipment being used, and the like. In general, parenteral dosages will range from about 0.001 to about 1.0 mmol of paramagnetic ion complex per kg of patient body weight. Preferred parenteral dosages generally range from about 0.01 to about 0.5 mmol of paramagnetic ion complex per kg of patient body weight. Enteral dosages generally range from about 0.5 to about 100 mmol, preferable from about 1.0 to about 10.0 mmol, preferable from about 1.0 to about 20.0 mmol of paramagnetic ion complex per kg of patient body weight.

The diagnostic compositions of the present invention are used in the conventional manner. The compositions may be administered to a patient, typically a warm-blooded animal, either systemically or locally to the organ or tissue to be imaged, and the patient then subject to the NMR imaging procedure. Protocols for imaging and instrument procedures are found in texts such as Stark, D. D.; Bradley, W. G. *Magnetic Resonance Imaging*; Mosby Year Book: St. Louis, Mo., 1992.

Radiopharmaceutical Imaging Procedures are found in Fred A. Mettler, Jr., M.D., M. P. H., Milton J. Guiberteau, M.D., *Essentials of Nuclear Medicine Imaging*, Grune and Stratton, Inc., New York, N.T. 1983) and E. Edmund Kin, M. S., M.D. and Thomas P. Haynie, M.D., (MacMillan Publishing Co., Inc, New York, N.Y. 1987).

XRCM Imaging Procedures are found in Albert A. Moss, M.D., Gordon Gamsu, M.D., and Harry K. Genant, M.D., *Computed Tomography of the Body*, (W. B. Saunders Company, Philadelphia, Pa., 1992) and M. Sovak, Editor, *Radiocontrast Agents*, (Springer-Verlag, Berlin 1984).

In another facet of the present invention, there is provided new ligands which have application (after complexing with, for example, a paramagnetic ion) in the MRI area. These ligands have the general formula (X)

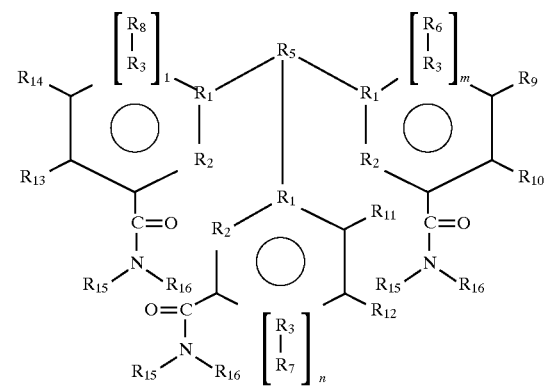

wherein $R_1$–$R_{16}$, l, m, and n are the same as set forth in formula (I) above.

A class of compounds (ligands) falling within formula (X) above are

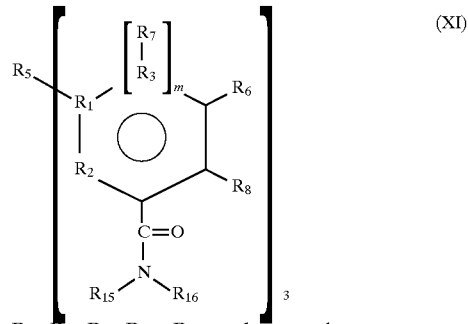

(XI)

wherein $R_1$–$R_3$, $R_5$–$R_8$, $R_{15}$, $R_{16}$ and m are the same as set forth in formula (X) above.

Sub-generic ligand formulae under formula (XI) above have, for example, the following structural formulae:

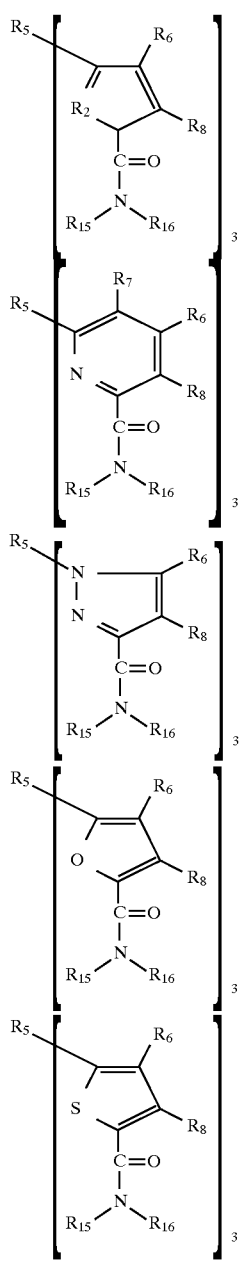
(XII)

(XIII)

(XIV)

(XV)

(XVI)

Examples of compounds falling within formulas (XI) are as follows:

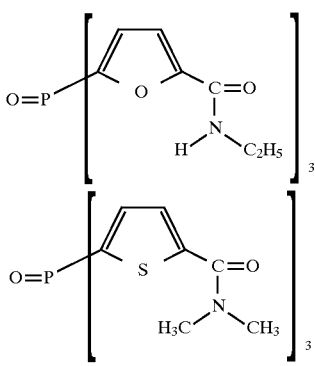

(XVII)

(XVIII)

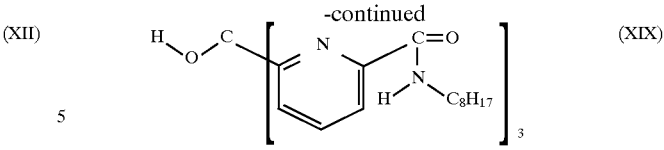

(XIX)

The novel ligands and the novel ligand-metal complexes of the present invention are prepared from substituted aromatic heterocycles ("SAH") which are generally commercially available from Aldrich Chemical Company (Milwaukee). The SAH have the general formula:

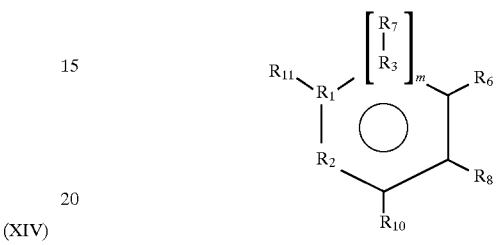

wherein $R_1$–$R_3$ and $R_6$–$R_8$ and m are defined above. $R_{10}$ and $R_{11}$ are defined below.

When m=1, these SAH are derivatives of pyridine in that $R_1$ and $R_3$=C, $R_2$=N, $R_{10}$=halogen or carboxylic group, and $R_{11}$=halogen.

When m=0, these SAH are derivatives of pyrazole in that $R_1$=C, $R_2$ is O or S, $R_{10}$ is a halogen or carboxylic acid groups and $R_{11}$ is a halogen.

$R_6$–$R_8$ are the same as defined above and are protected if incompatible with the reaction conditions.

For example when m=1 and $R_2$ is N, both $R_{10}$ and $R_{11}$ can be halogen (such as Br) and then a halogen lithium exchange reaction is carried out at low temperature (e.g. from about −100° C. to about −20° C.) to generate a monolithium reagent which is then coupled with a linking reagent such as diphenyl carbonate, to link three units of SAH to form a capping mode ligand in one or two steps as shown in Scheme 2. The other halogen atoms on the SAH are carbonylated to form the amide group $C(O)N(R_{15})(R_{16})$ in one or more steps, also show in Scheme 2.

In another example where m=0 and the starting material is a furan and where $R_{10}$ is a carboxylic acid and $R_{11}$ is halogen, $R_{10}$ is first protected by converting it to an oxazoline under amidation conditions as shown in Scheme 1, then, the amide is thus subjected to ring closure conditions to form the oxazoline. A halogen lithium exchange reaction is then carried out at low temperature to form a monolithium reagent which is coupled with a linking agent such as $POCl_3$, $PCl_3$ or methyl chloroformate, to link three units of SAH. The carboxylic acid groups are then regenerated and converted as shown to amides, $C(O)N(R_{15})(R_{16})$ as shown in Scheme 1.

The final step in the overall synthesis for preparing the ligand-metal complex is reaction of the novel ligand with a solution containing the metal ion in the form of a compound which, for example, may be the acetate form, e.g. $Gd(OCa)_3$. Pressures and temperatures are not critical. The mole ratio of ligand to metal (atom) is about 1:1.

Some examples of specific processes for preparing the novel compositions of the present invention are set forth in Schemes 1 and 2 and which, respectively, outline the detailed procedures described in Examples 1–5.

Scheme 1
Synthesis of Gadolinium Tri(2-carboxamide-5-furanyl)phosphine Oxide (GDTCFPO)

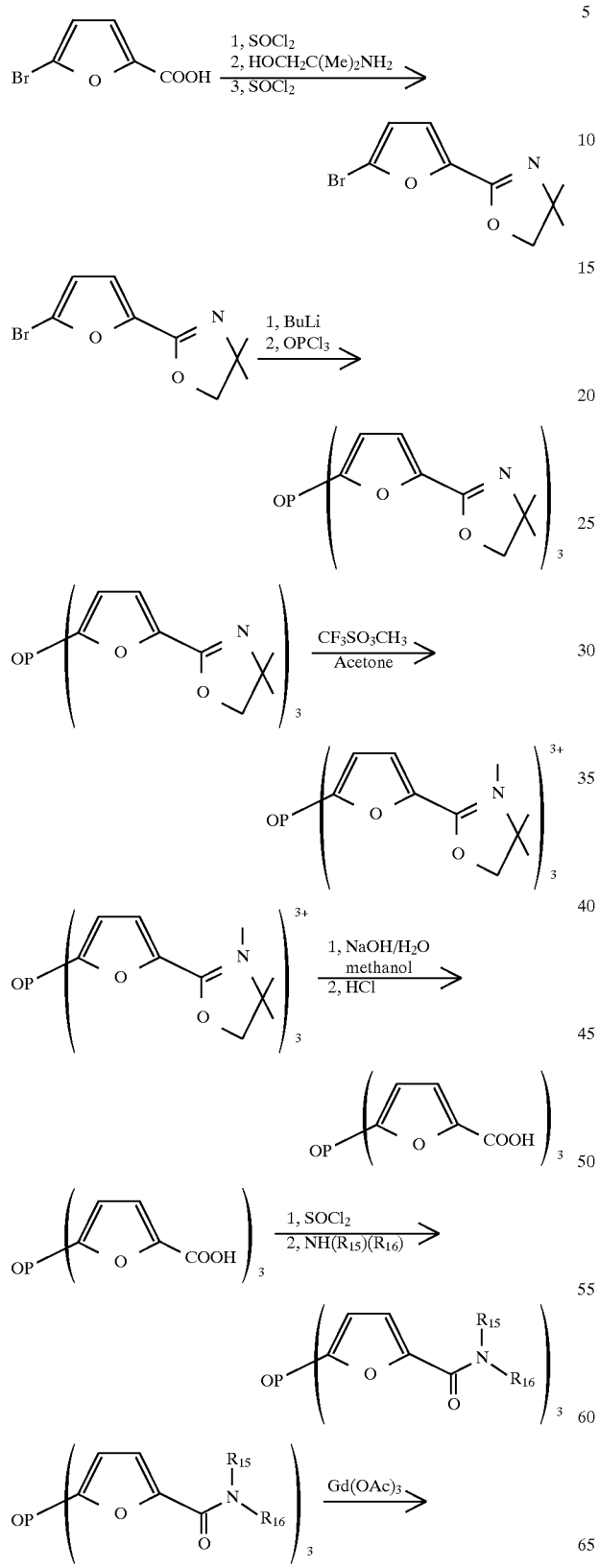

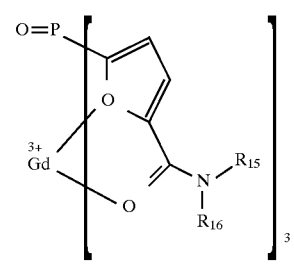

Scheme 2
Synthesis of Gadolinium Tris(2-carboxamide-6-pyridyl)methanol

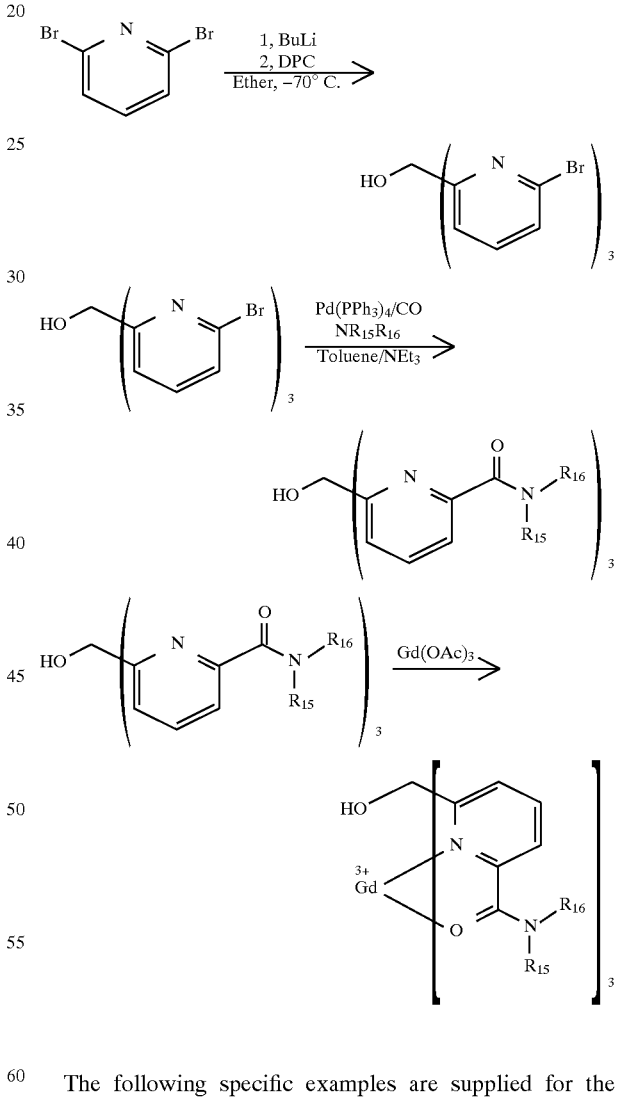

The following specific examples are supplied for the purpose of better illustrating the invention. These examples are not intended, However, to limit or restrict the scope of the invention in any way and should not be construed as providing conditions, parameters, or values which must be utilized exclusively in order to practice the present invention.

EXAMPLE 1

Synthesis of
tris)2-(n-octyl carboxamide)-6-pyridyl)methanol (TOCAPM)

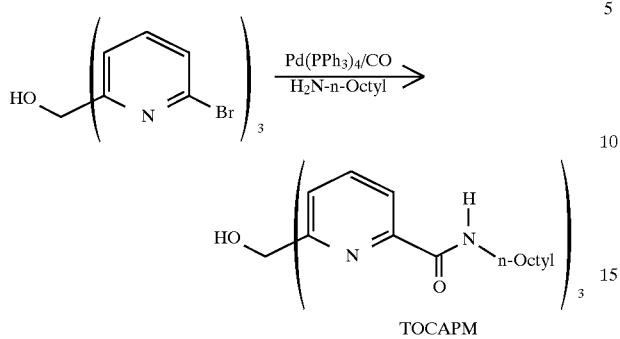

TOCAPM

Under nitrogen atmosphere, a toluene (150 ml) solution was prepared in a 250 ml flask containing tris(2-bromo-6-pyridyl)methanol (4.0 g, 8.0 mmol), n-octylamine (12.4 g, 96.0 mmol), palladium tetrakis(triphenylphosphine)(0.69 g, 0.6 mmol), triethylamine (8.0 g, 79.1 mmol). This solution was charged into a 300 ml stainless steel reactor under nitrogen. The reactor was pressurized with CO to 150 psi and then pressure was released. This procedure was repeated twice. The reactor was then pressurized to 450 psi, started to heat to a target temperature of 100° C., and stirred at 750 rpm. The pressure was adjusted to 500 psi when the temperature reached 100° C. After 48 hours, a sample was analyzed on HPLC and the result showed that the starting material was completely consumed. Reactor was cooled to room temperature, CO released and reactor purged with nitrogen three times. Reaction solution was transferred to a flash and volatile removed on a rotary evaporator to obtain a yellow slurry. Hexane (100 ml) was added causing formation of solid. Hexane was decanted and solid washed twice with hexane. A waxy yellow solid was obtained. The yield was about 90%. This material contains small amounts of triphenylphosphine and n-octylamine hydrobromide. $^1$H NMR (400 MHZ, CDCl$_3$) 8.14 (d, J$_{H-H}$=7.6 Hz, Py H), 7.87 (t, J$_{H-H}$=7.6 Hz, Py H), 7.74 (d, J$_{H-H}$=7.6 Hz, Py H), Peaks for protons on amide nitrogen atoms and n-octyl groups are from 3.37 to 0.85. $^{13}$C NMR (100 MHZ, CDCl$_3$) 163.5, 160.7, 148.1, 137.9, 125.4, 121.3, 81.63, 39.41, 31.71, 29.43, 29.12, 29.11, 26.84, 22.54, 13.97.

EXAMPLE 2

Synthesis of Gadolinium
tris(2-(n-octyl carboxamide)-6-pyridyl)methanol (GdTOCAPM)

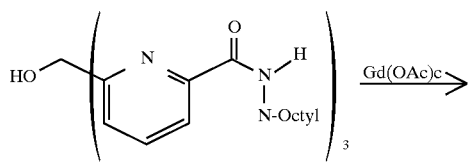

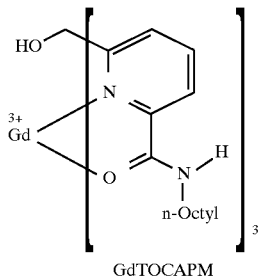

GdTOCAPM

TOCAPM (1.00 g, 1.3 mmol) was dissolved in 50 ml of ethanol. Gd(OAc)$_3$ (0.52 g, 1.3 mmol), dissolved in 50 ml of ethanol and 10 ml of water, was added to the TOCAPM solution. The resulting solution was stirred at 65° C. for two hours and then filtered. The volume of the filtrate was reduced to 20 ml and water (50 ml) was then added to cause precipitation of white solid, which was filtered and dried to give 0.7 g product.

EXAMPLE 3

Synthesis of
tri(2-(n-octyl carboxamide)-6-pyridyl)phosphine (TOCAPP)

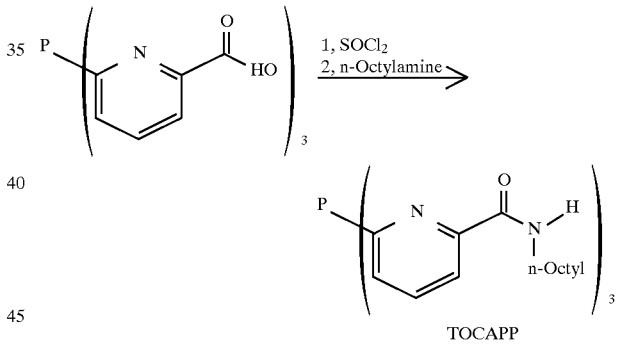

TOCAPP

A solution of tris(2-carboxy-6-pyridyl)phosphine (1.92 g, 4.1 mmole) in 20 mL of thionyl chloride under an inert nitrogen atmosphere was allowed to reflux for two hours. The thionyl chloride was then distilled off leaving an off white solid which was dried under vacuum. The solid was then dissolved in 20 mL dry THF under an inert atmosphere. The solution was then cooled in an ice bath and freshly distilled octyl amine (6 mL, 36.3 mmol) was added. The reaction was allowed to warm to room temperature with stirring overnight and the reaction mixture was then poured onto 50 mL of brine and extracted three times with 50 mL portions of THF. The organic layers were combined and the solvent removed under reduced pressure to give a viscous red oil. The crude product was dissolved in boiling methanol and decolorizing carbon added, followed by a hot filtration. The solvent was again removed under reduced pressure at a final temperature of 75° C., producing 0.7 g viscous oil.

EXAMPLE 4

Synthesis of gadolinium tris(2-(n-octyl carboxamide)-6-pyridyl)phosphine (GdTOCAPP)

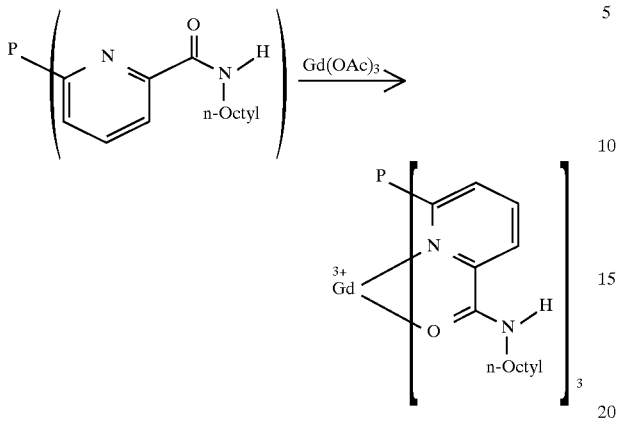

GdTOCAPP was synthesized in the similar procedure as described in Example 2.

Although the invention has been utilized by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A composition of matter having the formula

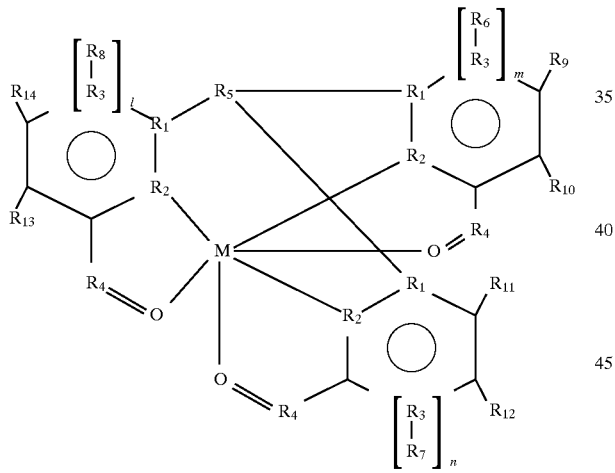

wherein l, m and n are 1

$R_1$ is C or N $R_2$ is N, O, or S $R_3$ is C $R_4$ is C N $(R_{15})(R_{16})$ $R_5$ is selected from the group consisting of
(a) P
(b) P=O
(c) B(R)$^-$M'
(d) N
(e) N(CH$_2$)
(f) N[C(O)]$_3$
(g) N[CH$_2$C(O)]$_3$
(h) CH
(I) COR
(j) COC(O)N(R)$_2$
(k) C(CH$_2$OR)(CH$_2$)$_3$
(l) SiR wherein R is selected from the group consisting of
(I) H
(ii) $C_1$–$C_{20}$) alkyl
(iii) hydroxyalkyl ($C_1$–$C_{30}$)
(iv) CH$_2$CH(OH)CH$_2$(O CH$_2$CH(OH)CH$_2$)$_n$OH (n=0–10)
(v) CH$_2$CH$_2$(O CH$_2$CH$_2$)$_n$OH (n=0–10)
(vi) ribose
(vii) glucose
(viii) peptide or polypeptide
(ix) PO$_3$$^{2-}$2M' and M' is Na$^+$ or meglumine $R_6$–$R_{14}$ are each independently selected from the group consisting of
(a) R
(b) OR
(c) N(R)$_2$
(d) NHC(O)R
(e) COO$^-$M'
(f) C(O)N(R)$_2$
(g) SO$_3$$^-$M' wherein R and M' are defined as above, and

M is a suitable metal ion, with the proviso that $R_{15}$ and $R_{16}$ are each the same as R defined above, except (ix), and $R_{15}$ and $R_{16}$, respectively, are each the same on each ring.

2. A composition of matter having the formula

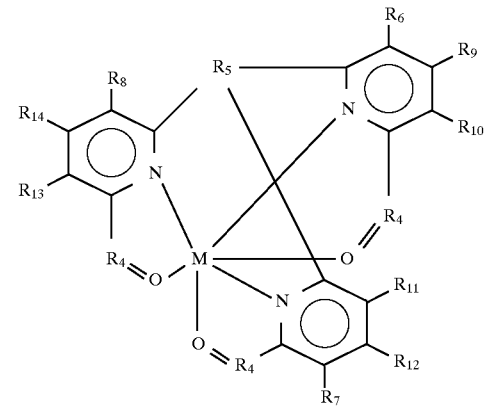

wherein:

$R_4$ is C N $(R_{15})(R_{16})$ $R_5$ is selected from the group consisting of
(a) P
(b) P=O
(c) N
(d) N(CH$_2$)
(e) N[C(O)]$_3$
(f) N[CH$_2$C(O)]$_3$
(g) CH
(h) COR
(I) COC(O)N(R)$_2$ wherein R is selected from the group consisting of
(I) H
(ii) $C_1$–$C_{20}$ alkyl
(iii) hydroxyalkyl ($C_1$–$C_{30}$)
(iv) CH$_2$CH$_2$(OH)CH$_2$(O CH$_2$CH(OH)CH$_2$)$_n$OH (n=0–10)
(v) CH$_2$CH$_2$(O CH$_2$CH$_2$)$_n$OH (n=0–10)

(vi) ribose
(vii) glucose
(viii) peptide or polypeptide
(ix) $PO_3^{2-}2M'$
and M' is $Na^+$ or meglumine $R_6$–$R_{14}$ are each independently selected from the group consisting of
(a) R
(b) OR
(c) $N(R)_2$
(d) NHC(O)R
(e) $COO^-M'$
(f) $C(O)N(R)_2$
(g) $SO_3^-M'$
wherein R and M' are defined as above, and
M is a suitable metal ion, with the proviso that $R_{15}$ and $R_{16}$ are each the same as R defined above, except (ix), and $R_{15}$ and $R_{16}$ respectively, are each the same on each ring.

3. A composition having the formula

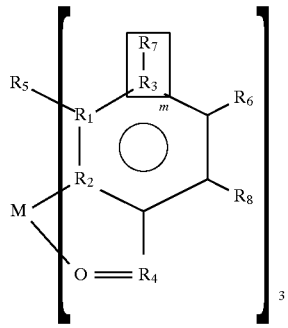

wherein
m is 1
$R_1$ is C or N
$R_2$ is N, O, or S
$R_3$ is C
$R_4$ is C N $(R_{15})(R_{16})$
$R_5$ is selected from the group consisting of
(a) P
(b) P=O
(c) $B(R)^-M'$
(d) N
(e) $N(CH_2)$
(f) $N[C(O)]_3$
(g) $N[CH_2C(O)]_3$
(h) CH
(I) COR
(j) $COC(O)N(R)_2$
(k) $C(CH_2OR)CH_2)_3$
(l) SiR
wherein R is selected from the group consisting of
(I) H
(ii) $C_1$–$C_{20}$ alkyl
(iii) hydroxylalkyl ($C_1$–$C_{20}$)
(iv) $CH_2CH_2(OH)$ $CH_2(OCH_2CH(OH)CH_2)_nOH$ (n=0–10)
(v) $CH_2CH$ (O $CH_2CH_2)_nOH$ (n=0–10)
(vi) ribose
(vii) glucose
(viii) peptide or polypeptide
(ix) $PO_3^{2-}2M'$, and
M' is $Na^+$ or meglumine $R_{6-R8}$ is selected from the group consisting of (a) R
(b) OR
(c) $N(R)_2$
(d) NHC(O)R
(e) $COO^-M'$
(f) $C(O)N(R)_2$
(g) $SO_3^-M'$
wherein R and M' are defined as above, and
M is a metal ion of the lanthanide series having an atomic number 57–71 or of a transition metal of an atomic number of 21.29, 42, or 44,
with the proviso that $R_{15}$ and $R_{16}$ are each the same as R defined above, except (ix), and $R_{15}$ and $R_{16}$, respectively, are each the same on each ring.

4. The composition as set forth in claim 3 wherein $R_1$=C and $R_2$=N.

5. The composition as set forth in claim 4 wherein $R_4$ is C N (H)($C_8H_{17}$).

6. The composition as set forth in claim 3 wherein M is selected from the group consisting of chromium (III), manganese (II), iron (III), iron (II), cobalt (II), nickel (II), copper, (II), praseodymium (III), neodymium (III), samarium (II), ytterbium (III), gadolinium (III), terbium (III), dysprosium (III), holmium (III), erbium (III), lanthanum (III), gold (III), lead (II), bismuth (III), lutetium (III), and europium (III).

7. The composition as set forth in claim 3 wherein M is gadolinium (III).

8. A composition of matter having the formula

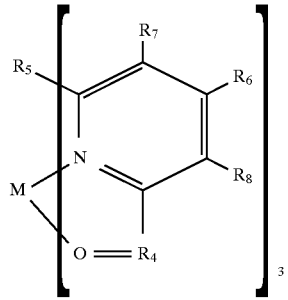

wherein:
$R_4$ is C N $(R_{15})(R_{16})$
$R_5$ is selected from the group consisting
(a) P
(b) P=O
(c) N
(d) $N(CH_2)$
(e) $N[C(O)]_3$
(f) $N[CH_2C(O)]_3$
(g) CH
(h) COR
(I) $COC(O)N(R)_2$
wherein R is selected from the group consisting of
(I) H
(ii) $C_1$–$C_{20}$ alkyl
(iii) hydroxylalkyl ($C_1$–$C_{20}$)
(iv) $CH_2CH(OH)CH_2(O$ $CH_2CH(OH)CH_2)_nOH$ (n=0–10)
(v) $CH_2CH(O$ $CH_2CH_2)_nOH$ (n=0–10)
(vi) ribose
(vii) glucose
(viii) peptide or polypeptide
(ix) $PO_3^{2-}2M'$
and M' is $Na^+$ or meglumine $R_6$ to $R_8$ are each independently selected from the group consisting of (a) R
(b) OR
(c) $N(R)_2$
(d) NHC(O)R
(e) $COO^-M'$
(f) $C(O)N(R)_2$
(g) $SO_3^-M'$ wherein R and M' are defined as above, and M is a metal ion of the lanthanide series having an atomic number 57–71 or of a transition metal of an atomic number of 21–29, 42, or 44, with the proviso that $R_{15}$ and $R_{16}$ are each the same as R defined above, except (ix), and $R_{15}$ and $R_{16}$, respectively, are each the same on each ring.

9. The composition as set forth in claim 8 wherein M is selected from the group consisting of chromium (III), manganese (II), iron (III), iron (II), cobalt (II), nickel (II), copper (II), praseodymium (III), neodymium (III), samarium (III), ytterbium (III), gadolinium (III), terbium (III), dysprosium (III), holmium (III), erbium (III), lanthanum (III), gold (III), lead (II), bismuth (III), lutetium (III) and europium (III).

* * * * *